United States Patent [19]
Lavielle et al.

[11] Patent Number: 4,946,833
[45] Date of Patent: Aug. 7, 1990

[54] N-(23-VINBLASTINOYL)COMPOUNDS OF 1-AMINOMETHYLPHOSPHONIC ACID USEFUL FOR TREATING NEOPLASTIC DISEASES

[75] Inventors: Gilbert Lavielle, La Celle St-Cloud; Patrick Hautefaye, Sevron Brie Comte Robert; Claude Cudennec, La Celle St-Cloud, all of France

[73] Assignee: Adir et Cie, Neuilly-sur-Seine, France

[21] Appl. No.: 276,357

[22] Filed: Nov. 23, 1988

[30] Foreign Application Priority Data

Nov. 25, 1987 [FR] France ................. 87 16327

[51] Int. Cl.⁵ ................. A61K 31/475; C07D 519/04; C07F 9/6561
[52] U.S. Cl. ......................... 514/81; 540/478
[58] Field of Search ................. 540/478; 514/283, 81

[56] References Cited

U.S. PATENT DOCUMENTS

| | | | |
|---|---|---|---|
| 3,097,137 | 7/1963 | Beer | 540/478 X |
| 3,205,220 | 9/1965 | Svoboda | 540/478 X |
| 3,749,784 | 7/1973 | Johnson | 514/283 |
| 4,203,898 | 5/1980 | Cullinan et al. | 540/478 |
| 4,208,414 | 6/1980 | Schinitsky | 514/283 |
| 4,639,456 | 1/1987 | Trouet et al. | 514/283 |
| 4,831,038 | 5/1989 | Trouet et al. | 514/283 |

FOREIGN PATENT DOCUMENTS

| | | |
|---|---|---|
| 659112 | 8/1965 | Belgium . |
| 0041935 | 12/1981 | European Pat. Off. . |
| 2415980 | 10/1974 | Fed. Rep. of Germany . |
| 2366020 | 4/1978 | France . |
| 0013593 | 1/1983 | Japan ................. 558/170 |
| 8300486 | 2/1983 | World Int. Prop. O. . |

OTHER PUBLICATIONS

Drug Evaluations, 6th Edition, American Medical Association, pp. 1180–1183, and 1203–1205 (09/86).
Goodman and Gilman's "The Pharmacological Basis of Therapeutics", Seventh Edition, pp. 1279 (1985).
Proceedings of The American Association for Cancer Research, vol. 30, Mar. 1989, 581, Preclinical Pharmacology and Experimental Therapeutics, 2311.

*Primary Examiner*—Diana G. Rivers
*Attorney, Agent, or Firm*—Gordon W. Hueschen

[57] ABSTRACT

The invention relates to N-(23-vinblastinoyl)compounds of 1-aminomethylphosphonic acid of general formula I

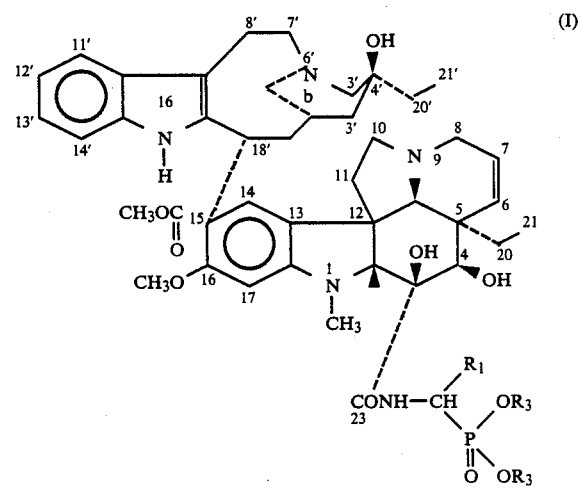

in which:

$R_1$ denotes a hydrogen atom, a linear or branched alkyl radical containing from 1 to 6 carbon atoms, a linear or branched alkylene radical containing from 1 to 6 carbon atoms, an arylalkyl radical having 7 to 10 carbon atoms and capable of bearing a halogen atom as a substituent on the aromatic ring, a hydroxyl radical or an alkyl or alkoxy radical each containing from 1 to 5 carbon atoms, a 2-indolylmethyl radical, a 4-imidzolylmethyl radical or an alkoxycarbonylmethyl radical containing from 3 to 11 carbon atoms, $R_2$ and $R_3$, which may be identical or different, each denote a linear or branched alkyl radical containing from 1 to 4 carbon atoms, in the form of a mixture of diastereoisomers or of pure isomers, their $N^{b'}$-oxides and their addition salts with a pharmaceutically acceptable inoranic or organic acid.

These compounds are antitumor agents.

8 Claims, No Drawings

N-(23-VINBLASTINOYL)COMPOUNDS OF 1-AMINOMETHYLPHOSPHONIC ACID USEFUL FOR TREATING NEOPLASTIC DISEASES

The present invention relates to new N-(23-vinblastinoyl). compounds of 1-aminomethylphosphonic acid, to processes for preparing them and to pharmaceutical compositions containing them.

Bisindole alkaloids of the vinblastine type, and some of their derivatives obtained by chemical conversion of natural alkaloids, are known in the literature and used in therapy, mainly in anticancer chemotherapy (U.S. Pat. Nos. 3,097,137 and 3,205,220 and Belgian Patents 659,112 and 813,168).

In effect, compounds such as vinblastine, vincristine and vindesine find their applications in the treatment of leukemias and some solid tumors. However, these compounds possess high toxicity.

With the object of obtaining compounds having lower toxicity and greater antitumor activity, some aminated N-(4-O-deacetyl-23-vinblastinoyl) compounds, such as vindesine, have been prepared (Belgian Patent 813,168). More recently, it has been found that N-(23-vinblastinoyl) derivatives of amino aicds or peptides, and more especially vintriptol, are endowed with very advantageous activity with respect to L 1210 leukemia and to P 388 experimental tumors, and have lower toxicity (European Application 041,935). Some derivatives of vinblastine and thiophosphonic acid are also known (French Application No. 77/19,877 and European Application 083,600).

The Applicant has now discovered that certain N-(23-vinblastinoyl) compounds of 1-aminomethylphosphonic acid, of novel structure, possess very advantageous pharmacological properties. In effect, the compounds of the present invention are endowed with very much greater antitumor activity than all known derivatives of vinblastine. In addition, the observed toxicities are significantly lower than those of the reference products.

The subject of the present invention is more especially the N-(23-vinblastinoyl) compounds of 1-aminomethylphosphonic acid of general formula I:

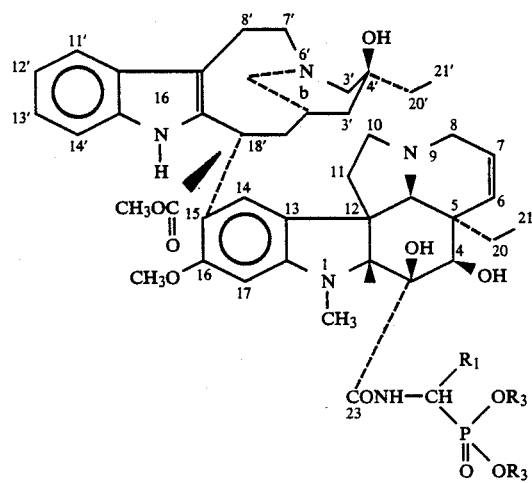

in which:
$R_1$ denotes a hydrogen atom, a linear or branched alkyl radical containing from 1 to 6 carbon atoms, a linear or branched alkylene radical containing from 1 to 6 carbon atoms, an arylalkyl radical having 7 to 10 carbon atoms and capable of bearing a halogen atom as a substituent on the aromatic ring, a hydroxyl radical or an alkyl or alkoxy radical each containing from 1 to 5 carbon atoms, a 2-indolylmethyl radical, a 4-imidazolylmethyl radical or an alkoxycarbonylmethyl radical containing from 3 to 11 carbon atoms, $R_2$ and $R_3$, which may be identical or different, each denote a linear or branched alkyl radical containing from 1 to 4 carbon atoms, in the form of a mixture of diastereoisomers or of pure isomers, their $N^{b'}$-oxides and their addition salts with a pharmaceutically acceptable inorganic or organic acid.

The subject of the present invention is also the process for preparing compounds of general formula I, wherein an amine, in racemic or optically pure form, of general formula II:

in which the definition of $R_1$, $R_2$ and $R_3$ remains that defined above for the general formula I, is reacted with 3-decarbomethyoxy-4-O-deacetylvinblastine-3-carboxazide of formula III

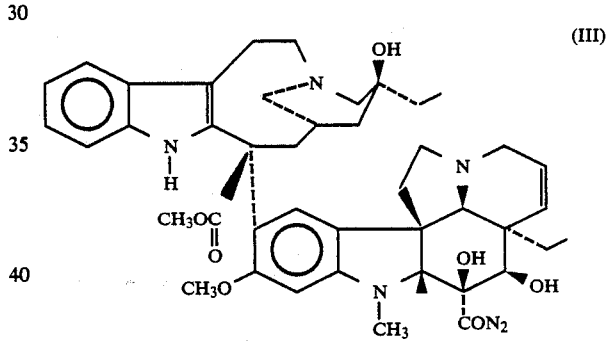

to form, in the form of a mixture of diastereoisomers or of pure isomers, respectively, the compounds of general formula I, which compounds can then:
either be salified with a pharmaceutically acceptable inorganic or organic acid,
or be converted to the corresponding $N^{b'}$-oxides using a basic organic solvent saturated with oxygen.

1-Aminomethylphosphonates, the compounds of general formula II, may be prepared according to three processes:
either by reduction by means of zinc of the compounds of general formula IV:

in which $R_1$, $R_2$ and $R_3$ have the meaning defined above for the formula I, in solution in formic acid; or by alkylation of the imines of general formula V:

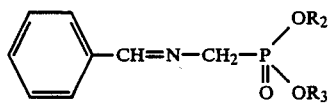 (V)

in which $R_2$ and $R_3$ have the meaning defined above for the formula I,
by means of an alkyl halide of general formula VI:

$$R_1X \quad (VI)$$

in which the definition of $R_1$ remains identical to that given for the formula I, according to the method described in Bull. Soc. Chim. Fr. (1978), II, p. 95;
or by the action of diphenylphosphoryl azide (DPPA) on acids of general formula VII:

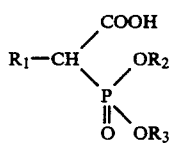 (VII)

in which $R_1$, $R_2$ and $R_3$ have the meaning defined above for the formula I,
to form the carbamates of general formula VIII:

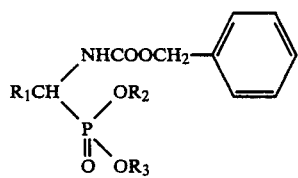 (VIII)

in which the definition of $R_1$, $R_2$ and $R_3$ remains identical to that given for the formula I,
which are then subjected to a catalytic hydrogenolysis to form the amines of general formula II [Tetrahedron Letters, (1983), 24, (49), p. 5461].

The compounds of general formula IV are obtained by the action of hydroxylamine on the ketones of general formula IX:

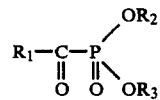 (IX)

in which $R_1$, $R_2$ and $R_3$ have the meaning defined above for the formula I, according to the process described in Synthesis, (1981), p. 57. The preparation of the compounds of general formula IX is known (Houben Weyl, Methoden der Organischen Chemie, Georg Thiene Verlag, Stuttgart, 5th ed, vol. 12/1, p. 453).

The preparation of the compounds of general formula V is described in Tetrahedron Letters, (1973), 46, p. 4645.

3-Decarbomethoxy-4-O-deacethylvinblastine-3-carboxazide, the compound of formula III, is prepared in two stages [J. Med. Chem., (1978), 21, p. 88]. The first stage consists in adding an excess of anhydrous hydrazine to a solution of vinblastine base in anhydrous methanol. The compound obtained, of formula X:

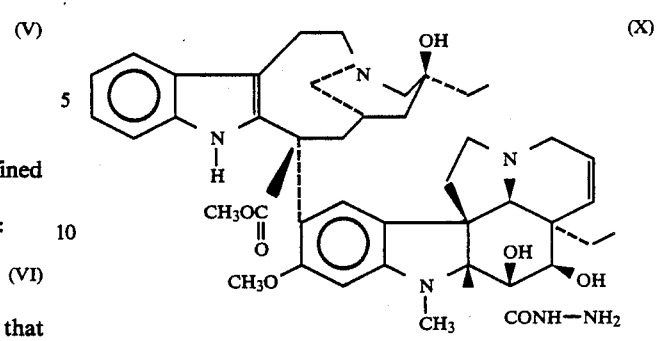 (X)

is then subjected to the action of sodium nitrite in acid medium, to form 3-decarbomethoxy-4-O-deacetylvinblastine-3-carboxazide, the compound of formula III.

The acid used in this last reaction can be hydrochloric acid. The temperature of the reaction medium is maintained at between 0° and 5° C.

The 3-decarbomethoxy-4-O-deacetylviblastine-3-carboxazide formed is then extracted with a water-insoluble aprotic solvent, preferaly methylene chloride. The compound of formula III is preferably not isolated. In effect, the organic solution containing it is concentrated, and the compound of formual III is then brought into contact at room temperature with the 1-aminomethylphosphonic acid derivatives of general formula II.

The amines of general formula II may be obtained optically pure, either by fractional crystallization of their salts with an optically pure acid [J. Org. Chem., (1963), 28, p. 2493], or according to the process described in Liebigs Ann. Chem., (1987), p. 45.

The compounds of general formula I may also be obtained in the form of pure diastereoisomers by condensation of 3-decarbomethoxy-4-O-deacetylvinblastine-3-carboxazide with an optically pure amine of general formula II or from a mixture of diastereoisomers which are then separated by high pressure liquid chromatography (HPCL).

The compounds of general formula I are 3-decarbomethoxy-4-O-deacetylvinblastine-3-carboxamide derivatives. Nevertheless, it is preferable to designate them an N-(23-vinblastinoyl) derviatives of 1-aminomethylphosphonic acid.

Among pharmaceutically acceptable acids for the preparation of addition salts with the compounds of general formula I, there may be mentioned phosphoric, hydrochloric, citric, oxalic, maleic, sulfuric, tartaric, mandelic, fumaric and methanesulfonic acids, and the like.

The compounds according to the invention, as well as their addition salts, are endowed with highly advantageous pharmacological properties, and are distinguished from other, already known N-(23-vinblastinoyl) compounds of amino acids.

The compounds of the invention were tested for their capacity to prolong the survival of mice bearing tumor cells (P 388 and L 1210), intraperitoneally according to the protocols recommended by the US National Cancer Institute [Geran R. I. et al., Cancer Chemotherapy Reports, (1972), III, 3, No. 2, p. 1–87], and recognized as representing the antitumor effect in human clinical medicine [Driscoll J. S. Cancer Treatment Reports, (1984), 68, No. 1, p. 63–85 and "In vivo cancer Models" US Department of Health and Human Services NIH Publication No. 84–2635 Feb. 1984].

The compounds of the present invention proved capable not only of slowing down the growth of grafted tumors in mice, but also of curing leukemic animals. In effect, many complete remissions were observed. In addition, comparative tests with reference products described in the literature—vinblastine and vintriptol—demonstrated that the compounds of the invention have very much greater activity compared with already known compounds.

The compounds of the present invention are useful in man and animals in cases of Hodgkin's disease, non-Hodgkin's lymophomas, cancers of the testicle, epithelioma of the breast and the ovary, Kaposi's sarcoma, choriocarcinoma, histiocytosis, rhabdomyosarcomas, neuroblastomas, Wilm's tumors, Ewing's sarcomas, and the like. Other therapeutic applications may also be envisaged for the compounds of the invention. In effect, it is known that bisindole alkaloids and their derivatives are active for the treatment of certain types of arthritis or of psoriasis (U.S. Pat. Nos. 4,208,414 and 3,749,784).

The invention also extends to the pharmaceutical compositions containing, as active principle, at least one compound of general formula I, one of its optical isomers or one of its addition salts with an inorganic or ogranic acid, with one or more non-toxic and suitable inert excipients.

The pharmaceutical compositions thereby obtained are advantageously presented in various forms such as, for example, tablets, dragees, hard gelatin capsules, creams for local application, suppositories, injectable solutions, and the like. They can contain doses of 0.1 to 100 mg of one or more compounds of the invention.

For their therapeutic application, the compounds of the invention, their optical isomers or their addition salts are preferably administered parenterally. Generally speaking, the compounds of the invention may be used according to procedures based on the techniques and limitations which are known for therapeutic treatments with other alkaloids of the Vinca class.

The dosage can vary widely according to the patient's age and weight, the nature and severity of the condition and the administration route, as well as the therapeutic scheme used. The total weekly doses will generally range from 0.05 to approximately 20 mg/kg.

The compounds of the invention may be used alone or in combination with one or more carcinostatic agents including, for example, alkylating agents, antimetabolites such as methotrexate, 5-fluorouracil, 6-mercaptopurine, 6-thioguanine and cytosine arabinosides and antibiotics such as actinomycin D, daunorubicine and adriamycin, and cis-diamminedichloroplatinum, and the like.

The examples which follow, given without implied limitation, illustrate the invention.

The proton nuclear magnetic resonance (NMR) spectra were recorded at 400 MHz.

The melting points stated are measured according to the micro-Kofler technique.

The mass spectra (FAB+ and FAB−) are obtained with a mass spectrometer having a quadripole filter, NERMAG ®10-10C.

Matrix: mixture of glycerol and thioglycerol (50V:50V).
  Instant gas: Krypton
  Energy: 6 to 8 keV.

The main fragments of the mass spectra of the compounds of Example 1-11 described below are shown in Table I.

EXAMPLE 1

Diethyl N-(4-O-deacetyl-23-vinblastinoyl)-1-amino-2-methyl-propylphosphonate 5.2 mmol of sodium nitrite are added to a solution of 130 ml of N hydrochloric acid, cooled to 0° C. and containing 2.34 mmol of 4-O-deacetyl-23-vinblastinoyl hydrazide. After 10 minutes' contact at 0° C., the pH of the medium is adjusted to 8.8 using ice-cold saturated sodium bicarbonate solution, and the mixture is extracted rapidly using four times 100 ml of dichloromethane. The combined organic phases are washed using saturated sodium chloride solution and dried over anhydrous magnesium sulfate. The organic phase is concentrated to a volume of 50 ml, 3.1 mmol of diethyl 1-amino-2-methylpropylphosphonate [Synthesis, (1981), 57] are added and the reaction medium is left for 24 hours at room temperature.

After evaporation of the solvent, the residue is purified by chromatography on a silica column (230–400 mesh), using a mixture of toluene and ethanol (80V:20V) as eluent.

0.67 g of product is collected, and crystallized in a mixture of ethyl ether and petroleum ether (50V:50V).
  Yield: 30%

Diethyl (+)-N-(40-O-deacetyl-23-vinblastinoyl)-1-amino-2-methylpropylphosphonate sulfate This compound is prepared according to the method described above, starting with 1.5 g of N-(4-O-deacetyl-23-vinblastinoyl) hydrazide and 0.65 of diethyl (+)-1-amino-2-methylpropylphosphonate.

After 24 hours' stirring at room temperature, the solvent is separated off to obtain 1.6 of product, which is dissolved in 4 ml of ethanol. This solution is then purified by chromatography, using a column containing 500 g of Lichoroprep RP 18 (15–25 μm). Elution is performed using a mixture of methanol and 0.1 M aqueous disodium hydrogen phosphate solution (70V:30V). The flow rate of the mobile phase is fixed at 20 ml/min. Fractions 620 to 800 are combined and, after evaporation under vacuum, the residue is extracted with methylene chloride, and then the organic phase is dried over anhydrous magnesium sulfate. After evaporation of the solvent, 0.55 g of diethyl (+)-N-(4-O-deacetyl-23-vinblastinoyl)-1-amino-2methyl-propylphosphonate is obtained, and then salified using 2% strength ethanolic sulfuric acid.
  Yield: 30%.

| Proton nuclear magnetic resonance spectrum (basis - solvent CDCl$_3$) | | | |
|---|---|---|---|
| 0.89 ppm,6H; | 1.81 ppm,1H; | 3.21 ppm,1H; | 4.29 ppm 1H; |
| 1.08 ppm,6H; | 2.10 ppm,2H; | 3.34 ppm,1H; | 4.33 ppm,1H; |
| 1.20 ppm,1H; | 2.30 ppm,2H; | 3.42 ppm,1H; | 5.68 ppm,1H; |
| 1.31 ppm,6H; | 2.38 ppm,1H; | 3.45 ppm,1H; | 5.81 ppm,1H; |
| 1.35 ppm,2H; | 2.53 ppm,1H; | 3.59 ppm,3H; | 6.09 ppm,1H; |
| 1.42 ppm,1H; | 2.79 ppm,3H; | 3.76 ppm,3H; | 6.57 ppm,1H; |
| 1.50 ppm,1H; | 2.80 ppm,2H; | 3.95 ppm,1H; | 7.13 ppm,3H; |
| 1.64 ppm,1H; | 2.83 ppm,1H; | 4.13 ppm,2H; | 7.47 ppm,1H; |
| 1.80 ppm,1H; | 3.13 ppm,1H; | 4.18 ppm,1H; | 7.51 ppm,1H; |

Diethyl (−)-N-(4-O-deacetyl-23-vinblastinoyl)-1-amino-2-methylpropylphosphonate sulfate This compound is obtained according to the process described for diethyl (+)-N-(4-O-deacetyl-23-vinblastinoyl)-1-amino-2-methylpropylphosphonate sulfate, but using diethyl (−)-1-amino-2-methylpropylphosphonate.

During the purification by chromatographyl, fractions 400 to 500 are combined and treated as described above.

Yield: 29%

| Proton nuclear magnetic resonance spectrum (basis - solvent CDCl₃) | | | |
|---|---|---|---|
| 0.89 ppm,3H; | 2.05 ppm,1H; | 3.24 ppm,1H; | 4.41 ppm,1H; |
| 0.93 ppm,3H; | 2.18 ppm,1H; | 3.35 ppm,1H; | 5.74 ppm,1H; |
| 1.00 ppm,6H; | 2.28 ppm,2H; | 3.45 ppm,1H; | 5.84 ppm,1H; |
| 1.25 ppm,1H; | 2.41 ppm,1H; | 3.59 ppm,3H; | 6.07 ppm,1H; |
| 1.34 ppm,8H; | 2.56 ppm,1H; | 3.77 ppm,3H; | 6.58 ppm,1H; |
| 1.45 ppm,1H; | 2.81 ppm,1H; | 3.96 ppm,1H; | 7.10 to 7.13 ppm,3H; |
| 1.50 ppm,1H; | 2.83 ppm,5H; | 4.16 ppm,2H; | 7.40 ppm,1H; |
| 1.67 ppm,1H; | 3.13 ppm,2H; | 4.20 ppm,2H; | 7.52 ppm,1H. |
| 1.79 ppm,1H | | | |

EXAMPLES 2-11

The compound of Examples 2 to 11 in the form of a mixture of diastereoisomers were prepared according to the process described in Example 1, using the appropriate alkyl 1-aminomethylphosphonate derivatives.

EXAMPLE 2

Diethyl N-(4-O-deacetyl-23-vinblastinoyl)-1-amino-ethylphosphonate

Alkyl 1-aminomethylphosphonate derivative used: diethyl 1-aminoethylphosphonate

Yield: 30%

Diethyl (−)-N-(4-O-deacetyl-23-vinblastinoyl)-1-aminoethylphosphonate sulfate

This compound is obtained according to the process described for diethyl (−)-N-(4-O-deacetyl-23-vinblastinoyl)-1-amino-2-methyl-propylphosphonate sulfate and using diethyl (−)-1-amino-ethylphosphonate. During the purification by chromatography, the fractions selected are: 164 to 209.

| Proton nuclear magnetic resonance spectrum (basis - solvent CDCl₃) | | | |
|---|---|---|---|
| 0.896 ppm,3H; | 2.29 ppm,1H; | 3.33 ppm,1H; | 4.47 ppm,1H; |
| 0.94 ppm,3H; | 2.44 ppm,1H; | 3.43 ppm,1H; | 5.79 ppm,1H; |
| 1.25 ppm,1H; | 2.59 ppm,1H; | 3.60 ppm,3H; | 5.84 ppm,1H; |
| 1.34 ppm,6H; | 2.84 ppm,3H; | 3.75 ppm,1H; | 6.07 ppm,1H; |
| 1.38 ppm,3H; | 2.87 ppm,1H; | 3.77 ppm,3H; | 6.57 ppm,1H; |
| 1.73 ppm,2H; | 3.14 ppm,1H; | 3.95 ppm,1H; | 7.10 to 7,15 ppm,3H; |
| 2.03 ppm,1H; | 3.23 ppm,1H; | 4.17 ppm,2H; | 7.52 ppm,1H. |

Mass spectrum: (Matrix 50V:50V mixture of glycerol and thioglycerol—bombarding atoms: xenon). FAB⁺(m/z): 932 (M+14+1); 918 (M+1); 900; 886; 858; 709; 542; 355; 337; 323; 295; 154; 144; 122; 108. FAB⁻(m/z): 930 (M+14+1); 916 (M−1); 914; 898; 888; 886; 870; 858; 778; 760; 178; 152; 137.

Diethyl (+)-N-(4-O-deacetyl-23-vinblastinoyl)-1-aminoethylphosphonate sulfate This compound is obtained according to the process described for diethyl (+)-N-(4-O-deacetyl-23-vinblastinoyl)-1-amino-2-methylpropylphosphonate sulfate, and using diethyl (+)-1-aminoethylphosphonate. During the purification, the fractions collected are: 221 to 256.

| Proton nuclear magnetic resonance spectrum (basis - solvent CDCl₃) | | | |
|---|---|---|---|
| 0.89 ppm,3H; | 2.03 ppm,1H; | 3.21 ppm,1H; | 4.20 ppm,1H; |
| 0.92 ppm,3H; | 2.29 ppm,1H; | 3.33 ppm,1H; | 4.50 ppm,1H; |
| 1.23 ppm,1H; | 2.42 ppm,1H; | 3.39 ppm,1H; | 5.72 ppm,1H; |
| 1.30 ppm,1H; | 2.57 ppm,1H; | 3.59 ppm,3H; | 5.82 ppm,1H; |
| 1.32 ppm,6H; | 2.78 ppm,3H; | 3.77 ppm,3H; | 6.08 ppm,1H; |
| 1.40 ppm,2H; | 2.80 ppm,1H; | 3.78 ppm,1H; | 6.57 ppm,1H; |
| 1.43 ppm,3H; | 2.83 ppm,1H; | 3.95 ppm,1H; | 7.10 to 7.15 ppm,3H; |
| 1.68 ppm,1H; | 3.14 ppm,1H; | 4.14 ppm,2H; | 7.51 ppm,1H |
| 1.77 ppm,1H | | | |

Mass spectrum: (Matrix 50V:50V mixture of glycerol and thioglycerol—bombarding atoms: xenon). FAB⁺(m/z): 932 (M+14+1); 918 (M+1); 900; 886; 858; 651; 649; 571; 355; 337; 323; 295; 154; 144; 122; 108. FAB⁻(m/z): 930 (M+14+1); 916 (M−1); 914; 888; 886; 870; 858; 840; 778; 760; 178; 152; 137.

EXAMPLE 3

Diethyl N-(4-O-deacetyl-23-vinblastinoyl)-1-aminohexylphosphonate

Alkyl 1-aminomethylphosphonate derivative used: diethyl 1-aminohexylphosphonate.

Yield: 35%.

To form the corresponding sulfate, diethyl N-(4-O-deacetyl-23-vinblastinoyl)-1-aminohexylphosphonate is salified using 2% strength ethanolic sulfuric acid. The salt formed is precipitated by adding ethyl ether.

Melting point: 200° C.

EXAMPLE 4

Diethyl N-(4-O-deacetyl-23-vinblastinoyl)-1-amino-3-methylbutylphosphonate

Alkyl 1-aminomethylphosphonate derivative used: diethyl 1-amino-3-methylbutylphosphonate.

Yield: 31%.

To form the corresponding sulfate, this compound is then dissolved in 2% strength alcoholic sulfuric acid and the salt formed is precipitated using ethyl ether.

Melting point: 202°-206° C. (decomposition).

EXAMPLE 5

Diethyl N-(4-O-deacetyl-23-vinblastinoyl)-1-amino-3-butenylphosphonate

Alkyl 1-aminomethylphosphonate derivative used: diethyl 1-amino-3-butenylphosphonate.

Yield: 25%.

Diethyl N-(4-O-deacetyl-23-vinblastinoyl)-1-amino-3-butenylphosphonate sulfate was prepared according to the salification process described above.

Melting point: 196°-200° C.

Separation of the mixture of diastereoisomers of diethyl N-(4-O-deacetyl-23-vinblastinoyl)-1-amino-3-butenylphosphonate A 20% strength solution of diethyl N-(4-O-deacetyl-23-vinblastinoyl)-1-amino-3-butenylphosphonate in ethanol containing 600 mg of product is chromatographed on a column containing 500 g of Lichroprep RP18 15–25μm, using a mixture of methanol and a 0.1M aqueous solution of disodium hydrogen phosphate (65V:35V) as elution solvent. The flow rate of the mobile phase is fixed at 20 ml/min and the volume of the fractions collected is 20 ml.

Diastereoisomer A

The fractions 90 to 130 are combined, the methanol is evaporated off under vacuum, the residue is extracted with methylene chloride, or the organic phase is dried over anhydrous magnesium sulfate, and the solvent is evaporated off to obtain the diastereoisomer A.

| Proton nuclear magnetic resonance spectrum (basis - solvent CDCl$_3$) | | | |
|---|---|---|---|
| 0.89 ppm,3H; | 2.41/2.62 ppm,2H; | 3.59 ppm,3H; | 6.07 ppm,1H; |
| 0.90 ppm,1H; | 2.41/3.22 ppm,2H; | 3.77 ppm,3H; | 6.57 ppm,1H; |
| 0.93 ppm,3H; | 2.41/3.41 ppm,2H; | 4.15 ppm,2H; | 7.14 ppm,2H; |
| 1.25/1,68 ppm,2H; | 2.58 ppm,1H; | 4.18 ppm,1H; | 7.34 ppm,1H; |
| 1.30 ppm,2H; | 2.82 ppm,5H; | 4.52 ppm,1H; | 7.52 ppm,1H; |
| 1.34 ppm,6H; | 2.85/3.35 ppm,2H; | 5.1 ppm,2H; | 8.03 ppm,1H; |
| 1.41/1,49 ppm,2H; | 3.12/3.30 ppm,2H; | 5.74 ppm,1H; | 9.55 ppm,1H. |
| 1.70/2,03 ppm,2H; | 3.12/3.68 ppm,2H; | 5.81 ppm,1H; | |
| 2.27/3,96 ppm,2H; | 3.44 ppm,1H; | 5.83 ppm,1H; | |

Diastereoisomer B

Fractions 170 to 220 are treated in the same manner to obtain the diastereoisomer B.

| Proton nuclear magnetic resonance spectrum (basis - solvent CDCl$_3$) | | | |
|---|---|---|---|
| 0.87 ppm,3H; | 2.53 ppm,1H; | | 4.49 ppm,1H; |
| 0.89 ppm,3H; | 2.75 ppm,3H; | | 5.10 ppm,2H; |
| 0.90 ppm,1H | 2.8/3,3 ppm,2H; | | 5.68 ppm,1H; |
| 1.22/1,64 ppm,2H; | 2.80 ppm,2H; | | 5.80 ppm,2H; |
| 1.30 ppm,6H; | 3.11/3.39 ppm,2H; | | 6.07 ppm,1H; |
| 1.35 ppm,2H; | 3.20/3.72 ppm,2H; | | 6.57 ppm,1H; |
| 1.48 ppm,2H; | 3.34 ppm,1H; | | 7.10 ppm,2H; |
| 1.78/2.02 ppm,2H; | 3.57 ppm,3H; | | 7.32 ppm,1H; |
| 2.40/2.70 ppm,2H; | 3.75 ppm,3H; | | 7.50 ppm,1H; |
| 2.40/3.95 ppm,2H; | 4.14 ppm,2H; | | 8.02 ppm,1H; |
| 2.40/3.39 ppm,2H; | 4.20 ppm,1H; | | 9.57 ppm,1H. |

EXAMPLE 6

Diethyl N-(4-O-deacetyl-23-vinblastinoyl)-1-amino-2-phenylethylphosphonate

Alkyl 1-aminomethylphosphonate derivative used: diethyl 1-amino-2-phenylethylphosphonate.
Yield: 40%.

To form diethyl N-(4-O-deacetyl-23-vinblastinoyl)-1-amino-2-phenylethylphosphonate sulfate, the amine was salified using 2% strength alcoholic sulfuric acid according to the process described above.

Melting poing: 199° C.

Separation of mixture of diastereoisomers of diethyl N-(4-O-deacetyl-23-vinblastinoyl)-1-amino-2-phenylethylphosphonate The diastereoisomers of diethyl N-(4-O-deacetyl-23-vinblastinoyl)-1-amino-2-phenylethylphosphonate were obtained according to the method described in Example 5. Elution solvent: mixture of methanol and a 0.1M aqueous solution of disodium hydrogen phosphate (70V:30V).

Diastereoisomer A

This compound is obtained via fractions 120 to 165.

| Proton nuclear magnetic resonance spectrum (basis - solvent CDCl$_3$) | | | |
|---|---|---|---|
| 0.87 ppm,1H; | 2.4/3.22 ppm,2H; | 3.42 ppm,1H; | 6.04 ppm,1H; |
| 0.9 ppm,6H; | 2.4/3.4 ppm,2H; | 3.58 ppm,3H; | 6.57 ppm,1H; |
| 1.21/1.66 ppm,2H; | 2.57 ppm,1H; | 3.75 ppm,3H; | 7.10 ppm,1H |
| 1.31 ppm,2H; | 2.78 ppm,3H; | 4.01 ppm,1H; | 7.15 ppm,2H, |
| 1.32 ppm,3H; | 2.83/3.34 ppm,2H; | 4.12 ppm,2H; | 7.20 ppm,1H; |
| 1.38/1.5 ppm,2H; | 2.83 ppm,2H; | 4.70 ppm,1H; | 7.28 ppm,2H; |
| 1.74/2.02 ppm,2H; | 2.90/3.4 ppm,2H; | 5.73 ppm,1H; | 7.30 ppm,2H; |
| 2.26/3.95 ppm,2H; | 3.15/3.29 ppm,2H; | 5.83 ppm,1H; | 7.53 ppm,1H; |

Diastereoisomer B

This compound is obtained via fractions 245 to 300.

| Proton nuclear magnetic resonance spectrum (basis - solvent CDCl$_3$) | | | |
|---|---|---|---|
| 0.84 ppm,1H; | 2.80/3.30 ppm,2H; | | 4.68 ppm,1H; |
| 0.88 ppm,3H; | 2.80/3.40 ppm,2H; | | 5.67 ppm,1H; |
| 0.89 ppm,3H; | 2.81 ppm,2H; | | 5.80 ppm,1H; |
| 1.15/1.60 ppm,2H; | 3.11/3.30 ppm,2H; | | 5.91 ppm,1H; |
| 1.32 ppm,5H; | 3.11/3.65 ppm,2H; | | 6.52 ppm,1H; |
| 1.45 ppm,2H; | 3.46 ppm,1H; | | 7.11 ppm,1H; |
| 1.72/1.91 ppm,2H; | 3.56 ppm,3H; | | 7.16 ppm,2H; |
| 2.23/3.94 ppm,2H; | 3.71 ppm,3H; | | 7.25 ppm,2H; |
| 2.39/3.21 ppm,2H; | 4.04 ppm,1H; | | 7.34 ppm,1H; |
| 2.39/3.39 ppm,2H; | 4.17 ppm,2H; | | 7.51 ppm,1H; |
| 2.51 ppm,1H; | | | |

EXAMPLE 7

Dimethyl N-(4-O-deacetyl-23-vinblastinoyl)-1-amino-2-(3-indolyl)ethylphosphonate Alkyl 1-aminomethylphosphonate derivative used: dimethyl 1-amino-2-(3-indolyl)ethylphosphonate. The latter compound was synthesized according to the method described in Tetrahedron Letters, (1983), 24, p. 5461.

Yield: 47%.

EXAMPLE 8

Diethyl (+)-N-(4-O-deacetyl-23-vinblastinoyl)-1-amino-2-(3-indolyl)ethylphosphonate

STAGE A

Diethyl (+)-1-amino-2-(3-indolyl)ethylphosphonate: 0.024 mol of diethyl 1-amino-2-(3-indolyl)ethylphosphonate, prepared according to the process described in Tetrahedron Letters, (1983), 24, p. 5461, are diluted in 25 ml of absolute ethanol. 50 ml of absolute ethanol containing 0.024 mol of (—)-dibenzoyltartaric acid monohydrate are added. After the reaction medium has been stirred for one hour, the precipitate formed is filtered off, washed with ethanol and dried under vacuum. After recrystallization in absolute ethanol, a salt whose melting point is 217°–218° C. is obtained.

This salt is suspended in methylene chloride 25% strength ammonia solution is then added dropwise until a pH equal to 9 is obtained.

The organic phase is then separated off after settling has occurred and dried over anhydrous magnesium sulfate. After evaporation of the solvent, 1.6 g of the expected product are obtained in the form of an oil.

Yield: 80%.

Rotary power: $\alpha_D^{22} = +18.6°$ (1% strength solution in $CHCl_3$).

STAGE B

Diethyl (+)-N-(4-O-deacetyl-23-vinblastinoyl)-1-amino-2-(3-indolyl)ethylphosphonate is obtained according to the process described in Example 1, using 1.95 mmol of 4-O-deacetyl-23-vinblastinoyl hydrazide and 2 mmol of the compound obtained in the preceding stage.

Yield: 55%.

| Proton nuclear magnetic resonance spectrum (basis - solvent $CDCl_3$) | | | | |
|---|---|---|---|---|
| 0.88 ppm, 6H; | 1.60 ppm, 2H; | 2.63 ppm,1H; | 3.46 ppm,1H; | 5.78 ppm,1H; |
| 0.92 ppm, 1H; | 1.64 ppm, 3H; | 2.70 ppm,1H; | 3.55 ppm,3H; | 5.83 ppm,1H; |
| 1.13 ppm, 1H; | 1.72 ppm, 1H; | 2.83 ppm,1H; | 3.64 ppm,3H; | 6.46 ppm,1H; |
| 1.31 ppm, 2H; | 2.24 ppm, 1H; | 3.14 ppm,1H; | 3.95 ppm,2H; | 7.12 ppm,1H; |
| 1.32 ppm, 2H; | 2.38 ppm, 1H; | 3.20 ppm,1H; | 4.18 ppm,4H; | 7.47 ppm,1H; |
| 1.34 ppm, 2H; | 2.40 ppm, 1H; | 3.30 ppm,2H; | 4.67 ppm,1H; | 7.97 ppm,1H; |
| 1.35 ppm, 1H; | 2.47 ppm, 1H; | 3.45 ppm,1H; | 5.67 ppm,1H; | 9.49 ppm,1H; |
| 1.47 ppm, 1H; | | | | |

Diethyl (+)-N-(4-O-deacetyl-23-vinblastinoyl)-1-amino-2-(3-indolyl)ethylphosphonate sulfate was prepared according to the method described in J. Med. Chem., (1978), 21, p. 96, after adding 4.35 ml of 2% strength ethanolic sulfuric acid. The salt is precipitated using ethyl ether.

Melting point: 220°–228° C. (decomposition).

EXAMPLE 9

Diethyl (—)-N-(4-O-deacetyl-23-vinblastinoyl)-1-amino-2-(3-indolyl)ethylphosphonate

STAGE A

Diethyl (—)-1-amino-2-(3-indolyl)ethylphosphonate: This compound was prepared according to the process described in Example 10, Stage A, but using (+)-dibenzoyltartaric acid instead of its levorotatory isomer.

Yield: 82%.

Rotatory power: $\alpha_D^{22} = -18°$ (1% strength solution in $CHCl_3$).

STAGE B

Diethyl (—)-N-(4-O-deacetyl-23-vinblastinoyl)-1-amino-2-(3-indolyl)ethylphosphonate was prepared from 1.95 mmol of 4-O-deacetylvinblastinoyl hydrazide and 2 mmol of the compound obtained in the preceding stage.

Yield: 54%.

| Proton nuclear magnetic resonance spectrum (basis - solvent $CDCl_3$) | | | | |
|---|---|---|---|---|
| 0.81 ppm, 3H; | 1.51 ppm, 1H; | 3.28 ppm,1H; | 4.17 ppm,4H; | 7.15 ppm,1H; |
| 0.85 ppm, 3H; | 2.81 ppm, 3H; | 3.37 ppm,1H; | 4.79 ppm,1H; | 7.50 ppm,1H; |
| 1.15 ppm, 2H; | 2.83 ppm, 1H; | 3.42 ppm,1H; | 5.60 ppm,1H; | 7.99 ppm,1H; |
| 1.33 ppm, 6H; | 2.86 ppm, 2H; | 3.56 ppm,3H; | 5.80 ppm,1H; | 8.50 ppm,1H; |
| 1.37 ppm, 1H; | 3.08 ppm, 1H; | 3.73 ppm,3H; | 6.01 ppm,1H; | 9.50 ppm,1H. |

Diethyl (—)-N-(4-O-deacetyl-23-vinblastinoyl)-1-amino-2-(3-indolyl)ethylphosphonate sulfate was obtained after adding an appropriate amount of 2% strength ethanolic sulfuric acid.

Melting point: 198°–202° C. (decomposition).

EXAMPLE 10

Diethyl N-(4-O-deacetyl-23-vinblastinoyl)aminomethylphosphonate

Alkyl 1-aminomethylphosphonate derivative used: diethyl aminomethylphosphonate.

Yield: 30%.

Diethyl N-(4-O-deacetyl-23-vinblastinoyl)aminomethylphosphonate sulfate was obtained after adding 2% strength ethanolic sulfuric acid.

Melting point: 194°–204° C. (decomposition).

EXAMPLE 11

Diethyl N-(4-O-deacetyl-23-vinblastinoyl)-1-amino-2-carboethoxyethylphosphonate

Alkyl 1-aminomethylphosphonate derivative used: diethyl 1-amino-2-carboethoxyethylphosphonate.

Yield: 47%.

The corresponding sulfate was obtained by adding 2% strength ethanolic sulfuric acid, as described above.

Melting point: 208°–210° C. (decomposition).

EXAMPLE 12

Diethyl N-(4-O-deacetyl-23-vinblastinoyl)-1-aminoethylphosphonate $Nb'$-oxide

Diethyl (—)-N-(4-O-deacetyl-23-vinblastinoyl)-1-aminoethylphosphonate $N^{b'}$-oxide.

Diethyl (—)-N-(4-O-deacetyl-23-vinblastinoyl)-1-aminoethylphosphonate, the compound described in Example 2, is taken up in a mixture of ethyl ether and petroleum ether (50:50 V/V) saturated with oxygen. The crystalline product thereby obtained is then filtered off and dried.

Yield: 100%.

| Proton nuclear magnetic resonance spectrum (basis - solvent CDCl₃) | | | | |
|---|---|---|---|---|
| 0.76 ppm, 3H; | 1.63 ppm, 1H; | 2.85 ppm,3H; | 3.80 ppm,2H; | 4.25 ppm,1H; |
| 0.97 ppm, 3H; | 1.70 ppm, 2H; | 3.25 ppm,1H; | 4.00 ppm,1H; | 4.46 ppm,1H; |
| 1.10 ppm, 1H; | 2.05 ppm, 1H; | 3.30 ppm,1H; | 4.04 ppm,1H; | 5.72 ppm,1H; |
| 1.35 ppm, 3H; | 2.41 ppm, 1H; | 3.45 ppm,1H; | 4.10 ppm,1H; | 5.81 ppm,1H; |
| 1.39 ppm, 3H; | 2.50 ppm, 1H; | 3.67 ppm,3H; | 4.11 ppm,1H; | 6.06 ppm,1H; |
| 1.50 ppm, 1H; | 2.60 ppm, 1H; | 3.79 ppm,3H; | 4.17 ppm,2H; | 6.17 ppm,1H; |
| 1.60 ppm, 1H; | 2.74 ppm, 1H. | | | |

Diethyl (+)-N-(4-O-deacetyl-23-vinblastinoyl)-1-aminoethylphosphonate $N^{b'}$-oxide.

Diethyl (+)-N-(4-O-deacetyl-23-vinblastinoyl)-1-aminoethylphosphonate is treated according to the process described above to obtain diethyl N-(4-O-deacetyl-23-vinblastinoyl)-1-aminoethylphosphonate $N^{b'}$-oxide. Yield: 100%.

| Proton nuclear magnetic resonance spectrum (basis - solvent CDCl₃) | | | | |
|---|---|---|---|---|
| 0.74 ppm, 3H; | 1.58 ppm, 1H; | 2.70 ppm,1H; | 3.77 ppm,3H; | 4.49 ppm,1H; |
| 0.93 ppm, 3H; | 1.60 ppm, 2H; | 2.78 ppm,3H; | 3.78 ppm,1H; | 5.65 ppm,1H; |
| 1.05 ppm, 1H; | 1.70 ppm, 1H; | 3.20 ppm,2H; | 3.80 ppm,1H; | 5.77 ppm,1H; |
| 1.08 ppm, 1H; | 1.80 ppm, 1H; | 3.40 ppm,1H; | 4.00 ppm,2H; | 6.06 ppm,1H; |
| 1.30 ppm, 3H; | 2.03 ppm, 1H; | 3.60 ppm,1H; | 4.10 ppm,2H; | 6.16 ppm,1H; |
| 1.42 ppm, 3H; | 2.40 ppm, 2H; | 3.65 ppm,3H; | 4.15 ppm,2H; | |
| 1.50 ppm, 1H; | 2.56 ppm, 1H; | 3.70 ppm,1H; | 4.23 ppm,1H. | |

TABLE I

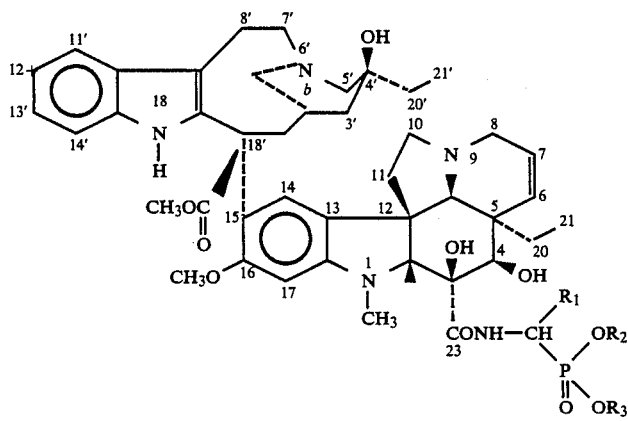

| COMPOUND | R₁ | R₂ | R₃ | MASS SPECTRUM (m/z) |
|---|---|---|---|---|
| Example 1 (mixture of diastereoisomers) | —CH(CH₃)₂ | —C₂H₅ | —C₂H₅ | FAB⁺: 946 (M + 1),709,651<br>FAB⁻: 944 (M − 1),926,916,806,180,152, 137,108 |
| Example 2 (mixture of diastereoisomers) | —CH₃ | —C₂H₅ | —C₂H₅ | FAB⁺: 932,918 (M + 1),900,886,872,858<br>FAB⁻: 930,916 (M − 1),898,888,858,137 |
| Example 3 | —C₅H₁₁ | —C₂H₅ | —C₂H₅ | FAB⁺: 974 (M + 1),914,836,651,649,632, 619,571,542,475,238,189,176,104<br>FAB⁻: 972 (M − 1),944,914,834,321,208, 196,190,180,154,137 |
| Example 4 | —CH₂—CH(CH₃)₂ | —C₂H₅ | —C₂H₅ | FAB⁺: 974,960, (M + 1),944,928,900, 709,651,649,604,571,542,355<br>FAB⁻: 958 (M − 1),930,820,137 |
| Example 5 (mixture of diasteroisomers) | —CH₂—CH=CH₂ | —C₂H₅ | —C₂H₅ | FAB⁺: 944 (M + 1),806,709,651,602,590, 571,542,355,295,272<br>FAB⁻: 942 (M − 1),137 |
| Example 6 (mixture of diastereoisomers) | —CH₂—C₆H₅ | —C₂H₅ | —C₂H₅ | FAB⁺: 994 (M + 1),962,934,856<br>FAB⁻: 992 (M − 1),964,854,137 |

TABLE I-continued

| COMPOUND | R$_1$ | R$_2$ | R$_3$ | MASS SPECTRUM (m/z) |
|---|---|---|---|---|
| Example 7 | —CH$_2$—(indole) | —CH$_3$ | —CH$_3$ | FAB$^+$: 1019,1-005 (M + 1),754,-752,651,355 |
| Example 8 | —CH$_2$—(indole) | —C$_2$H$_5$ | —C$_2$H$_5$ | FAB$^+$: 1033 (M + 1),709,679,651,571,542, 517,355,297 |
| Example 9 | —CH$_2$—(indole) | —C$_2$H$_5$ | —C$_2$H$_5$ | FAB$^+$: 1047,1033 (M + 1),709,691,679 651,571,542,355,295,272,130,124<br>FAB$^-$: 1031 (M − 1),1003 |
| Example 10 | H | —C$_2$H$_5$ | —C$_2$H$_5$ | FAB$^+$: 904 (M + 1),651,562,550,355 |
| Example 11 | —CH$_2$COOC$_2$H$_5$ | —C$_2$H$_5$ | —C$_2$H$_5$ | FAB$^+$: 990 (M + 1),752,651,649,571, 542,355<br>FAB$^-$: 988 (M − 1),960,752,662 |

PHARMACOLOGICAL STUDY

EXAMPLE 13

Antitumor activity with respect to P 388 leukemia in mice

Two groups of mice (n=6) of strain B$_6$D$_2$F$_1$ (F$_1$: C57Bl$_6$×DBA$_2$), of the same sex and age, received intraperitoneally, on day zero, 0.4 ml of physiological saline containing 10$^6$ leukemia cells in suspension. The test products were administered intravenously to the "test" groups one day after inoculation of the leukemia. The mortality of the animals in the "test" and "control" groups was recorded during 60 days after the inoculation. Table II shows the number of survivors noted after 30 days and 60 days of observation. After 60 days of observation, the animals which had survived were considered to be in long-term remission. Table III shows the percentage values for the mean survival time (MST) in the test groups T over the mean survival time in the untreated control group C. T/C (MST) values greater than 125% are indicative of an antitumor activity. The number of asterisks shown at each value corresponds to the number of survivors 60 days after the inoculation.

As demonstrated by the results in Tables II and III, the compounds of the invention possess better antitumor activity compared with the reference compounds vinblastine and vintriptol.

TABLE II

| | | SURVIVORS | | | |
|---|---|---|---|---|---|
| | | MALE | | FEMALE | |
| PRODUCTS | DOSE mg/kg | 30 DAYS | 60 DAYS | 30 DAYS | 60 DAYS |
| VINBLASTINE | 3.0 | | | 1/6 | 1/6 |
| | 5.0 | 1/6 | 1/6 | | |
| VINTRIPTOL | 80.0 | 1/6 | 0/6 | | |
| | 100.0 | 1/6 | 1/6 | 1/6 | 1/6 |
| EXAMPLE 1 | 0.25 | 2/6 | 2/6 | | |
| (mixture of | 0.4 | 3/6 | 1/6 | 3/6 | 3/6 |
| diastereo-isomers) | 0.6 | 3/6 | 3/6 | 4/6 | 4/6 |
| EXAMPLE 2 | 0.4 | | | 1/6 | 1/6 |
| (mixture of | 0.5 | 5/6 | 3/6 | 1/6 | 1/6 |
| diastero-isomers) | 0.6 | | | 2/6 | 2/6 |
| EXAMPLE 5 (mixture of diastero-isomers) | 1.0 | 1/6 | 1/6 | | |
| EXAMPLE 6 | 0.1 | | | 1/6 | 1/6 |

TABLE II-continued

| PRODUCTS | DOSE mg/kg | SURVIVORS MALE 30 DAYS | 60 DAYS | FEMALE 30 DAYS | 60 DAYS |
|---|---|---|---|---|---|
| (mixture of diastero-isomers) EXAMPLE 7 | 30 | 3/6 | 1/6 | 1/6 | 1/6 |
|  | 40 | 6/6 | 5/6 | 2/6 | 2/6 |
|  | 50 |  |  | 3/6 | 3/6 |
| EXAMPLE 10 | 3 | 1/6 | 1/6 |  |  |

TABLE III

| PRODUCTS | DOSE mg/kg | ANIMALS MALE | FEMALE |
|---|---|---|---|
| VINTRIPTOL | 40 | 167 |  |
|  | 60 | 174 | 180 |
|  | 80 | 240 | 208 |
|  | 100 | 246* | 215* |
| VINBLASTINE | 2 | 176 |  |
|  | 3 | 187 | 189* |
|  | 5 | 201* | 192 |
| EXAMPLE 1 (mixture of diastero-isomers) | 0.25 | 298** |  |
|  | 0.4 | 332* | 378*** |
|  | 0.6 | 395* | 395**** |
| EXAMPLE 2 (mixture of diastero-isomers) | 0.5 | 428*** | 233* |
|  | 0.6 |  | 324** |
| EXAMPLE 5 (mixture of diastero-isomers) | 1.0 | 278* |  |
| EXAMPLE 6 (mixture of diastero-isomers) | 0.1 |  | 184* |
| EXAMPLE 7 | 30 | 321* | 283 |
|  | 40 | 468***** | 350** |
|  | 50 |  | 416*** |
| EXAMPLE 10 | 3 | 239* |  |

EXAMPLE 14

Antitumor activity on L 1210 leukemia in mice

Two groups of mice (n=6) of strain $B_6D_2F_1$, of the same sex and age, received interperitoneally 0.4 ml of physiological saline containing $10^5$ leukemia cells (L 1210) in suspension. One day after inoculation of the leukemia, the test products were administered intraperitoneally to the "test" groups. The mortality was recorded in each experiment during 60 days after the inoculation. For each test, the number of survivors noted after 60 days and the percentage mean survival time in the test groups over the mean survival time in the untreated control group, MST T/C, are collated in Table IV. The results obtained in this study also demonstrate the pharmacological superiority of the compounds of the invention.

TABLE IV

| PRODUCTS | DOSE mg/kg | MST T/C | SURVIVORS |
|---|---|---|---|
| VINBLASTINE | 3 | 151 | 0/6 |
| VINTRIPTOL | 40 | 101 | 0/6 |
|  | 60 | 112 | 0/6 |
|  | 100 | 108 | 0/6 |
| EXAMPLE 2 (mixture of diastero-isomers) | 0.5 | 306 | 2/6 |
| EXAMPLE 5 (mixture of diastero-isomers) | 1.0 | 151 | 0/6 |
| EXAMPLE 7 | 80 | 242 | 1/6 |

Pharmaceutical Preparation

EXAMPLE 15

Lyophilized powder for an injectable preparation containing 0.5 mg of diethyl N-(4-O-deacetyl-23-vinblastinoyl)-1-amino-2-methyl-propylphosphonate

| | |
|---|---|
| Diethyl N-(4-O-deacetyl-23-vinblastinoyl)-1-amino-2-methylpropylphosphonate | 0.5 mg |
| Anhydrous lactose | 10 mg |
| for one vial of powder. | |

We claim:

1. A compound of formula I:

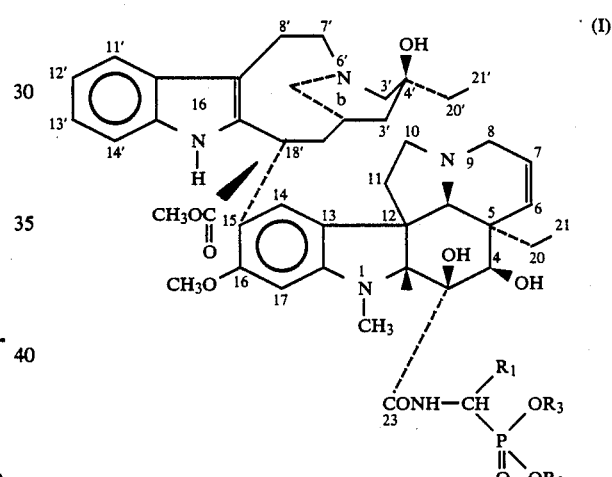

in which:

$R_1$ is a hydrogen atom, a linear or branched alkyl radical containing from 1 to 6 carbon atoms, a linear or branched alkylene radical containing from 1 to 6 carbon atoms, an arylalkyl radical having 7 to 10 carbon atoms and which may have a halogen atom as a substituent on the aromatic ring, a hydroxyl radical or an alkyl or alkoxy radical each containing from 1 to 5 carbon atoms, a 2-indolylmethyl radical, a 4-imidazolylmethyl radical or an alkoxycarbonylmethyl radical containing from 3 to 11 carbon atoms, $R_2$ and $R_3$, which may be identical or different, each are independently a linear or branched alkyl radical containing from 1 to 4 carbon atoms, in the form of a mixture of diastereoisomers or of pure isomers, their $N^{b'}$-oxides or an addition salt thereof with a pharmaceutically-acceptable inorganic or organic acid.

2. A compound as claimed in claim 1, in which:

$R_1$ is a linear or branched alkylene radical containing from 1 to 6 carbon atoms, and $R_2$ and $R_3$ are identical and represent a linear alkyl radical containing from 1 to 4 carbon atoms in the form of a mixture of diastereoisomers or of pure isomers, $N^{b'}$-oxides or an addition salt thereof with a pharmaceutically-acceptable inorganic or organic acid.

3. Compound of claim 1 being Diethyl N-(4-O-deacetyl-23-vinblastinoyl)-1-amino-2-methylpropylphosphonate, in the form of a mixture of diastereoisomers or of pure isomers, or an addition salt thereof with a pharmaceutically-acceptable inorganic or organic acid.

4. Compound of claim 1 being Diethyl N-(4-O-deacetyl-23-vinblastinoyl)-1-aminoethylphosphonate, in the form of a mixture of diastereoisomers or of pure isomers, or an addition salt thereof with a pharmaceutically-acceptable inorganic or organic acid.

5. A pharmaceutical composition containing as active principle a compound as claimed in any one of claims 1 to 4, inclusive, in combination or mixed with a pharmaceutically acceptable, non-toxic inert vehicle or excipient.

6. The pharmaceutical composition as claimed in claim 5, containing the active principle in an amount of 0.1 to 100 mg.

7. A method for the treatment of a neoplastic disease of a type known to be responsive to treatment with a vinca alkaloid in a living being comprising the step of administering to the living being an effective amount of a compound of any one of claims 1 to 4, inclusive, or a pharmaceutical composition of claim 5.

8. The method of claim 7 wherein a pharmaceutical composition is administered wherein the active compound is present in an amount of 0.1 to 100 mg.

* * * * *

UNITED STATES PATENT AND TRADEMARK OFFICE
CERTIFICATE OF CORRECTION

PATENT NO.   : 4,946,833

DATED        : Aug. 7, 1990

INVENTOR(S)  : Gilbert Lavielle, Patrick Hautefaye, Claude Cudennec

It is certified that error appears in the above-identified patent and that said Letters Patent is hereby corrected as shown below:

Title Page [57], ABSTRACT, line 10 after formula;
   "4-imidzolylmethyl" should read -- 4-imidazolylmethyl --.

Title Page [57], ABSTRACT, third line up from the bottom;
   "inoranic" should read -- inorganic --.

Column 3, line 63; "-deacethylvinblastine-" should read
   -- deacetylvinblastine- --.

Column 4, line 22; "-deacetylviblastine-" should read
   -- deacetylvinblastine- --.

Column 4, line 33; "2493]" should read -- 2483] --.

Column 4, line 45; "an" should read -- as --.

Column 5, line 12; "lymophomas," should read -- lymphomas, --.

Column 6, line 31; "-N-(40-O-" should read -- -N-(4-O- --.

Column 6, line 36; "0.65 of" should read -- 0.65 g of --.

Column 6, line 52; "-2methyl-" should read -- -2-methyl- --.

Column 17, line 25; "395*" should read -- 395 *** --.

Signed and Sealed this

Thirty-first Day of December, 1991

Attest:

HARRY F. MANBECK, JR.

Attesting Officer        Commissioner of Patents and Trademarks